US006872557B1

United States Patent
Ishizaki et al.

(10) Patent No.: US 6,872,557 B1
(45) Date of Patent: Mar. 29, 2005

(54) GENE ENCODING NOVEL HUMAN SECRETORY PHOSPHOLIPASE $A_2$

(75) Inventors: Jun Ishizaki, Osaka (JP); Noriko Suzuki, Osaka (JP); Kohji Hanasaki, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 379 days.

(21) Appl. No.: 10/088,092

(22) PCT Filed: Sep. 18, 2000

(86) PCT No.: PCT/JP00/06344

§ 371 (c)(1),
(2), (4) Date: Mar. 21, 2002

(87) PCT Pub. No.: WO01/21775

PCT Pub. Date: Mar. 29, 2001

(30) Foreign Application Priority Data

Sep. 21, 1999 (JP) .......................................... 11/266616

(51) Int. Cl.[7] .............................. C12N 9/20; C12N 1/20; C12N 15/00; C07H 21/04; C07K 1/00
(52) U.S. Cl. ................. 435/198; 435/252.3; 435/320.1; 536/23.2; 530/350
(58) Field of Search ............................ 435/198, 252.3, 435/320.1; 536/23.2; 530/350

(56) References Cited

U.S. PATENT DOCUMENTS 5,656,602 A * 8/1997 Tseng et al. .................. 514/17

OTHER PUBLICATIONS

Accession No. S17860.*
Accession No. AAR10126.*
Accession No. AAR63055, Accession No. U95301.*
Cupillard et al. [J. Biol. Chem. 272 (25): 15745–15752, Jun. 20 1997].*

J. Balsinde et al.: "Function and Inhibition of Intracellular calcium–independent phospholipase A2" J. Biol. Chem., vol. 272, No. 26, pp. 16069–16072 1997.

J.A. Tischfield et al.: "A reassessment of the low molecular weight phospholipase A2 gene family in mammals" J. Biol. Chem., vol. 272, No. 28, pp. 17247–17250 1997.

Jun Ishizaki et al.: "Cloning and characterization of novel mouse and human secretory phospholipase A2s" Journal of Biological Chemistry, vol. 274, No. 35, pp. 24973–24979.

Y. Yokota et al.: "Suppression of murine endotoxic shock by sPLA2 Inhibitor, indoxam, through group IIA sPLA2–independent mechanisms" Biochimica et Biophysica Acta, vol. 1438, No. 2, pp. 213–222, May 18, 1999.

E.D. Mihelich et al.: "Structure–based design of a new class of anti–inflammatory drugs: secretory phospholipase A2 Inhibitors, SPI" Biochimica et Biophysica Acta, vol. 1441, No. 2–3, pp. 223–228.

E. A. Dennis: "The growing phospholipase A2 supperfamily of signal transduction enzymes"0 Tibs Trends in Biochemical Sciences, vol. 22, No. 1, pp. 1–2 1997.

G. Lambeau et al.: "Receptors for a growing family of secreted phospholipase A2" Trends in Pharmacological Sciences, vol. 20, No. 4, pp. 162–170 Apr. 1999.

Nortiko Suzuki et al.: "Structures, enzymatic properties, and expression of novel human and mouse secretory phospholipase A2s" Journal of Biological Chemistry, vol. 275, No. 8, pp. 5785–5793 Feb. 25, 2000.

* cited by examiner

*Primary Examiner*—Tekchand Saidha
(74) *Attorney, Agent, or Firm*—Oblon, Spivak, McClelland, Maier & Neustadt, P.C.

(57) ABSTRACT

This invention relates to a gene encoding human secretory type phospholipase $A_2$ ($PLA_2$). According to the invention, an expression vector having this gene, and a transformant having the expression vector are obtainable. The $PLA_2$ protein can be produced by the culture of the transformant.

13 Claims, 2 Drawing Sheets

SEQUENCE LISTING

```
<160> NUMBER OF SEQ ID NOS: 34

<210> SEQ ID NO 1
<211> LENGTH: 320
<212> TYPE: DNA
<213> ORGANISM: Mus musculus
<220> FEATURE:
<221> NAME/KEY: misc_feature
```

```
<222> LOCATION: (11)..(11)
<223> OTHER INFORMATION: n = a, c, g, or t
<220> FEATURE:
<221> NAME/KEY: misc_feature
<222> LOCATION: (29)..(29)
<223> OTHER INFORMATION: n = a, c, g, or t
<220> FEATURE:
<221> NAME/KEY: misc_feature
<222> LOCATION: (38)..(38)
<223> OTHER INFORMATION: n = a, c, g, or t
<220> FEATURE:
<221> NAME/KEY: misc_feature
<222> LOCATION: (140)..(140)
<223> OTHER INFORMATION: n = a, c, g, or t
<220> FEATURE:
<221> NAME/KEY: misc_feature
<222> LOCATION: (295)..(295)
<223> OTHER INFORMATION: n = a, c, g, or t

<400> SEQUENCE: 1
cttcaagaga ngagggaaac ctgccctgna gtacaatnac tatggctgct attgcggtgt      60
cggtggctcc cactggccag tgggacgaaa cggattggtg ttgtcatgcc catgactgct     120 gctatgccg cctggagaan ctgggctgtg accccaagct ggaaaagtac ctcttctcta     180
tcactcgaga caacatcttc tgtgctggta aaacggcttg ccagcggcat acctgcgaat     240
gtgacaaaaa accgctctct gctttcgcca caacctgaac acttacaacc gcaantatgc    300
ccactacccc aacaagctgt                                                 320

<210> SEQ ID NO 2
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (11)..(11)
<223> OTHER INFORMATION: n = a, c, g, or t

<400> SEQUENCE: 2
cttcaagaga ngagggaaac ctg                                              23

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
agcttgttgg ggtagtgggc                                                  20

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 4
tcaagagang agggaaacct gcc                                              23

<210> SEQ ID NO 5
```

```
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
cttgttgggg tagtgggcat a                                              21

<210> SEQ ID NO 6
<211> LENGTH: 23
<212> TYPE: DNA
<213> ORGANISM: Artificial Sequence
<220> FEATURE:
<223> OTHER INFORMATION: Synthetic DNA

<400> SEQUENCE: 6
ggttgtaagt gttcaggttg tgg                                            23

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7
acattcgcag gtatgccgct g                                              21

<210> SEQ ID NO 8
<211> LENGTH: 22
<212> TYPE: DNA
<213> ORGANISM: Artificial Sequence
<220> FEATURE:
<223> OTHER INFORMATION: Synthetic DNA

<400> SEQUENCE: 8
agacaacatc ttctgtgctg gt                                             22

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA

<400> SEQUENCE: 9
ttgccagcgg catacctgcg agt                                            23

<210> SEQ ID NO 10
<211> LENGTH: 23
<212> TYPE: DNA
<213> ORGANISM: Artificial Sequence
<220> FEATURE:
<223> OTHER INFORMATION: Synthetic DNA

<400> SEQUENCE: 10
aggtagaaaa gagacctctc tca                                            23

<210> SEQ ID NO 11
<211> LENGTH: 22
<212> TYPE: DNA
<213> ORGANISM: Artificial Sequence
<220> FEATURE:
<223> OTHER INFORMATION: Synthetic DNA

<400> SEQUENCE: 11
```
tagacggtga ctcagagctg ca                                              22

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA

<400> SEQUENCE: 12
ggaaaataga cttctcttat tcag                                            24

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13
agggtattga gatgccagag gc                                              22

<210> SEQ ID NO 14
<211> LENGTH: 883
<212> TYPE: DNA
<213> ORGANISM: Mus musculus
<220> FEATURE:
<221> NAME/KEY: CDS
<222> LOCATION: (166)..(591)
<223> OTHER INFORMATION:
<220> FEATURE:
<221> NAME/KEY: mat_peptide
<222> LOCATION: (223)..()
<223> OTHER INFORMATION:

<400> SEQUENCE: 14
gaaaagagac ctctctcagt agacggtgac tcagagctgc agggtgtacc aggcaggtgg     60
actcggtccc catcaccttt gcaacaggga cagagcttgc agtacccaga tgcccctggg    120
aggtggcaga gcaggctccc atgcccctg cctacctccc ccagg atg aaa cct ccc    177
                                                 Met Lys Pro Pro att gcc ctg gct tgc ctt tgc ctc ctg gtg ccc ctg gct ggc ggg aac     225
Ile Ala Leu Ala Cys Leu Cys Leu Leu Val Pro Leu Ala Gly Gly Asn
-15              -10              -5              -1  1 ctg gtc cag ttt gga gtg atg att gag aga atg acg gga aag cct gcc     273
Leu Val Gln Phe Gly Val Met Ile Glu Arg Met Thr Gly Lys Pro Ala
          5               10              15 ctg cag tac aat gac tat ggc tgc tat tgc ggt gtc ggt ggc tcc cac     321
Leu Gln Tyr Asn Asp Tyr Gly Cys Tyr Cys Gly Val Gly Gly Ser His
     20              25              30 tgg cca gtg gac gag acg gat tgg tgt tgt cat gcc cat gac tgc tgc     369
Trp Pro Val Asp Glu Thr Asp Trp Cys Cys His Ala His Asp Cys Cys
 35              40              45 tat ggc cgc ctg gag aag ctg ggc tgt gac ccc aag ctg gaa aag tac     417
Tyr Gly Arg Leu Glu Lys Leu Gly Cys Asp Pro Lys Leu Glu Lys Tyr
50              55              60              65 ctc ttc tct atc act cga gac aac atc ttc tgt gct ggt aga acg gct     465
Leu Phe Ser Ile Thr Arg Asp Asn Ile Phe Cys Ala Gly Arg Thr Ala
         70              75              80 tgc cag cgg cat acc tgc gag tgt gac aag aga gct gct ctt tgc ttt     513
Cys Gln Arg His Thr Cys Glu Cys Asp Lys Arg Ala Ala Leu Cys Phe
     85              90              95 cgc cac aac ctg aac act tac aac cgc aag tat gcc cac tac ccc aac     561

```
                Arg His Asn Leu Asn Thr Tyr Asn Arg Lys Tyr Ala His Tyr Pro Asn
                        100                 105                 110 aag ctg tgt act ggg ccc acc cca ccc tgc tgaggccctg ctcggctcca            611
Lys Leu Cys Thr Gly Pro Thr Pro Pro Cys
        115                 120 tagccacccc aggctgctgc agtctcaggc ccagagaagc tcggaaccca gattcctctc        671
ccagcagact catcccgccc cccccccaga gatcatgagc cctggtctct ggcctccagg        731
accacaccag atccacggga tcagctgaag aagtcacggg actcgtcagc gctcacaaga       791
tccactaagt cgcctctggc atctcaatac cctcttctga ataagagaag tctatttttcc     851 cgaaaaaaaa aaaaaaaaaa aaaaaaaaaa aa                                    883

<210> SEQ ID NO 15
<211> LENGTH: 142
<212> TYPE: PRT
<213> ORGANISM: Mus musculus

<400> SEQUENCE: 15

Met Lys Pro Pro Ile Ala Leu Ala Cys Leu Cys Leu Val Pro Leu
                -15                 -10                  -5

Ala Gly Gly Asn Leu Val Gln Phe Gly Val Met Ile Glu Arg Met Thr
 -1   1                  5                  10

Gly Lys Pro Ala Leu Gln Tyr Asn Asp Tyr Gly Cys Tyr Cys Gly Val
        15                  20                  25

Gly Gly Ser His Trp Pro Val Asp Glu Thr Asp Trp Cys Cys His Ala
30                  35                  40                  45

His Asp Cys Cys Tyr Gly Arg Leu Glu Lys Leu Gly Cys Asp Pro Lys
                50                  55                  60

Leu Glu Lys Tyr Leu Phe Ser Ile Thr Arg Asp Asn Ile Phe Cys Ala
                65                  70                  75

Gly Arg Thr Ala Cys Gln Arg His Thr Cys Glu Cys Asp Lys Arg Ala
                80                  85                  90

Ala Leu Cys Phe Arg His Asn Leu Asn Thr Tyr Asn Arg Lys Tyr Ala
                95                 100                 105

His Tyr Pro Asn Lys Leu Cys Thr Gly Pro Thr Pro Pro Cys
110                 115                 120

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA

<400> SEQUENCE: 16
ctayggctgy yaytgygg                                                     18

<210> SEQ ID NO 17
<211> LENGTH: 19
<212> TYPE: DNA
<213> ORGANISM: Artificial Sequence
<220> FEATURE:
<223> OTHER INFORMATION: Synthetic DNA

<400> SEQUENCE: 17
gbycrtagca rcagtcatg                                                    19

<210> SEQ ID NO 18
<211> LENGTH: 300
```

```
<212> TYPE: DNA
<213> ORGANISM: Homo sapiens
<220> FEATURE:
<221> NAME/KEY: misc_feature
<222> LOCATION: (197)..(197)
<223> OTHER INFORMATION: n = a, c, g, or t

<400> SEQUENCE: 18
ctatggctgt tactgcggca tcggtggctc ccactggccg gtggaccaga ctgactggtg      60
aggaagcagc tgcagggggg acctccatgg ggatggagga gctgggggat cctgggagga     120
tcctgggaga aggagggaag cctgggggca cctggaaaat tcaggctgat ctctcctctg     180
ggctactttg ggctcgnggg ccccgagcag cccctggtcc agcccagcct ggctcacagg     240
tccctccagg tcaaccatga cccttgcagg tgctgccacg cccacgactg ctgctacggg     300

<210> SEQ ID NO 19
<211> LENGTH: 22
<212> TYPE: DNA
<213> ORGANISM: Artificial Sequence
<220> FEATURE:
<223> OTHER INFORMATION: Synthetic DNA

<400> SEQUENCE: 19
ctatggctgt tactgcggca tc                                               22

<210> SEQ ID NO 20
<211> LENGTH: 21
<212> TYPE: DNA
<213> ORGANISM: Artificial Sequence
<220> FEATURE:
<223> OTHER INFORMATION: Synthetic DNA

<400> SEQUENCE: 20
ggcatcggtg gctcccactg g                                                21

<210> SEQ ID NO 21
<211> LENGTH: 21
<212> TYPE: DNA
<213> ORGANISM: Artificial Sequence
<220> FEATURE:
<223> OTHER INFORMATION: Synthetic DNA

<400> SEQUENCE: 21
tcccactggc cggtggacca g                                                21

<210> SEQ ID NO 22
<211> LENGTH: 21
<212> TYPE: DNA
<213> ORGANISM: Artificial Sequence
<220> FEATURE:
<223> OTHER INFORMATION: Synthetic DNA

<400> SEQUENCE: 22
tagcagcagt cgtgggcgtg g                                                21

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA

<400> SEQUENCE: 23
tggcagcacc agtcagtctg                                                  20
```

```
<210> SEQ ID NO 24
<211> LENGTH: 21
<212> TYPE: DNA
<213> ORGANISM: Artificial Sequence
<220> FEATURE:
<223> OTHER INFORMATION: Synthetic DNA

<400> SEQUENCE: 24
agtctggtcc accggccagt g                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA

<400> SEQUENCE: 25
cccaaactga accaggttcc c                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic DNA

<400> SEQUENCE: 26
ggttcccggt gaccagagcc a                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic DNA

<400> SEQUENCE: 27
gctatggagc cgagcagggc c                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic DNA

<400> SEQUENCE: 28
ggggtggcta tggagccgag c                                              21

<210> SEQ ID NO 29
<211> LENGTH: 487
<212> TYPE: DNA
<213> ORGANISM: Homo sapiens
<220> FEATURE:
<221> NAME/KEY: CDS
<222> LOCATION: (59)..(484)
<223> OTHER INFORMATION:
<220> FEATURE:
<221> NAME/KEY: mat_peptide
<222> LOCATION: (116)..()
<223> OTHER INFORMATION:

<400> SEQUENCE: 29
ctgctttctt ctgctgcctt ttatgctcct tgtgcacctc ccttcccgc aacctggg      58
```

```
atg aaa tct ccc cac gtg ctg gtg ttc ctt tgc ctc ctg gtg gct ctg                   106
Met Lys Ser Pro His Val Leu Val Phe Leu Cys Leu Leu Val Ala Leu
        -15                 -10                 -5 gtc acc ggg aac ctg gtt cag ttt ggg gtg atg atc gag aag atg aca                   154
Val Thr Gly Asn Leu Val Gln Phe Gly Val Met Ile Glu Lys Met Thr
    -1  1                   5                   10 ggc aag tcc gcc ctg cag tac aac gac tat ggc tgt tac tgc ggc atc                   202
Gly Lys Ser Ala Leu Gln Tyr Asn Asp Tyr Gly Cys Tyr Cys Gly Ile
        15                  20                  25 ggt ggc tcc cac tgg ccg gtg gac cag act gac tgg tgc tgc cac gcc                   250
Gly Gly Ser His Trp Pro Val Asp Gln Thr Asp Trp Cys Cys His Ala
30                  35                  40                  45 cac gac tgc tgc tac ggg cgt ctg gag aag ctg ggc tgt gag ccc aaa                   298
His Asp Cys Cys Tyr Gly Arg Leu Glu Lys Leu Gly Cys Glu Pro Lys
                50                  55                  60 ctg gaa aag tat ctt ttc tct gtc agc gaa cgt ggc att ttc tgc gcc                   346
Leu Glu Lys Tyr Leu Phe Ser Val Ser Glu Arg Gly Ile Phe Cys Ala
                65                  70                  75 ggc agg acc acc tgc cag cgg ctg acc tgc gag tgt gac aag agg gct                   394
Gly Arg Thr Thr Cys Gln Arg Leu Thr Cys Glu Cys Asp Lys Arg Ala
            80                  85                  90 gcc ctc tgc ttt cgc cgc aac ctg ggc acc tac aac cgc aaa tat gcc                   442
Ala Leu Cys Phe Arg Arg Asn Leu Gly Thr Tyr Asn Arg Lys Tyr Ala
        95                  100                 105 cat tat ccc aac aag ctg tgc acc ggg ccc acc ccg ccc tgc tga                       487
His Tyr Pro Asn Lys Leu Cys Thr Gly Pro Thr Pro Pro Cys
110                 115                 120
```

<210> SEQ ID NO 30
<211> LENGTH: 142
<212> TYPE: PRT
<213> ORGANISM: Homo sapiens

<400> SEQUENCE: 30

```
Met Lys Ser Pro His Val Leu Val Phe Leu Cys Leu Leu Val Ala Leu
        -15                 -10                 -5

Val Thr Gly Asn Leu Val Gln Phe Gly Val Met Ile Glu Lys Met Thr
    -1  1                   5                   10

Gly Lys Ser Ala Leu Gln Tyr Asn Asp Tyr Gly Cys Tyr Cys Gly Ile
        15                  20                  25

Gly Gly Ser His Trp Pro Val Asp Gln Thr Asp Trp Cys Cys His Ala
30                  35                  40                  45

His Asp Cys Cys Tyr Gly Arg Leu Glu Lys Leu Gly Cys Glu Pro Lys
                50                  55                  60

Leu Glu Lys Tyr Leu Phe Ser Val Ser Glu Arg Gly Ile Phe Cys Ala
                65                  70                  75

Gly Arg Thr Thr Cys Gln Arg Leu Thr Cys Glu Cys Asp Lys Arg Ala
            80                  85                  90

Ala Leu Cys Phe Arg Arg Asn Leu Gly Thr Tyr Asn Arg Lys Tyr Ala
        95                  100                 105

His Tyr Pro Asn Lys Leu Cys Thr Gly Pro Thr Pro Pro Cys
110                 115                 120
```

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA

```
<400> SEQUENCE: 31
atgaaatctc cccacgtgct gg                                              22

<210> SEQ ID NO 32
<211> LENGTH: 49
<212> TYPE: DNA
<213> ORGANISM: Artificial Sequence
<220> FEATURE:
<223> OTHER INFORMATION: Synthetic DNA

<400> SEQUENCE: 32
agtagttgat gcggccgcca ccatgaaatc tccccacgtg ctggtgttc                 49

<210> SEQ ID NO 33
<211> LENGTH: 18
<212> TYPE: DNA
<213> ORGANISM: Artificial Sequence
<220> FEATURE:
<223> OTHER INFORMATION: Synthetic DNA

<400> SEQUENCE: 33
tcagcagggc ggggtggg                                                   18

<210> SEQ ID NO 34
<211> LENGTH: 44
<212> TYPE: DNA
<213> ORGANISM: Artificial Sequence
<220> FEATURE:
<223> OTHER INFORMATION: Synthetic DNA

<400> SEQUENCE: 34
taagcttttc tagatcagca gggcggggtg ggcccggtgc acag                      44
```

GENE ENCODING NOVEL HUMAN SECRETORY PHOSPHOLIPASE A$_2$

TECHNICAL FIELD

This invention relates to a human secretory type phospholipase A$_2$; a DNA encoding the protein; an expression vector having the DNA; a transformant having the vector; a method for producing the protein by using the transformant; an antibody recognizing the protein; a screening method for a compound by using the protein; and a compound obtained by the screening method.

BACKGROUND ART

Phospholipase A$_2$ (PLA$_2$; EC 3.1.1.4) is a general term of phospholipids-cleaving enzyme that hydrolyzes the 2-acyl ester bond of 3-sn-phosphoglyceride. PLA$_2$ is involved in the digestion of phospholipids in food and the generation and metabolism of phospholipids in the cell membranes. In addition, PLA$_2$ plays as a rate-limiting enzyme of the arachidonic acid cascade in the production of lipid mediators including prostaglandins. It has been known that various types of PLA$_2$s exist in mammals. PLA$_2$s are classified into 4 different families, such as the secretory PLA$_2$, cytosolic PLA$_2$, Ca$^{2+}$-independent PLA$_2$, and platelet-activating factor-acetylhydrolase, based on the localization, Ca$^{2+}$ requirement, and substrate specificity (Balsinde et al., J. Biol. Chem. 272, 16069–16072 (1997)).

Among them, secretory PLA$_2$ family comprises PLA$_2$ enzymes that are secreted into the outside of the cells and have a relatively low molecular weight (13,000–15,000). As the member of the family, 5 types including IB type, IIA type, IIC type, V type, and X type, have been already identified. Each molecule has 12 to 16 Cys residues that form disulfide-bonds in the molecule, and possesses a consensus active site consisting of His-Asp residues. In addition, the molecules have a common Ca$^{2+}$ binding region. Micro mole order of Ca$^{2+}$ concentration is required for the exertion of the enzymeactivity (Tischfield et al., J. Biol. Chem., 272, 17247–17250 (1997), Cupillard et al., J. Biol. Chem., 272, 15745–15752 (1997)).

It is assumed that IB type has a function as a digestive enzyme in the pancreas etc. and is involved in the progression of inflammation, such as endotoxin shock, through the binding to its specific receptor. It is also assumed that IIA type plays a role in various inflammatory responses because this type is expressed in blood platelets and synovial cells etc., and its expression is elevated during stimulation of inflammatory cytokines. However, the inflammatory response is normal in genetically IIA-deficient mice. Thus, its pathological significance remains unresolved. V type is expressed in the heart and several inflammatory cells. X type is expressed in the tissues related to the immunity such as spleen and thymus. Although it is suggested that both types are involved in the bio-regulation and inflammatory response, their importance in the body has not been clearly identified (Hanasaki et al., Cell Technology, 17, 694–701 (1998)).

DISCLOSURE OF INVENTION

The object of this invention is to provide a novel type of human secretory phospholipase A$_2$; a DNA encoding the protein of this invention; a vector comprising the DNA of this invention; a transformant having the vector of this invention; a method for producing human secretory type phospholipase A$_2$ by using the transformant of this invention; an antibody specifically recognizing the protein of this invention; a screening method of a compound by using the protein of this invention; and a compound obtained form the screening method.

In the process of intensive studies regarding the physiological function of mouse X type PLA$_2$, the inventors have found the presence of partial sequence with homology to mouse X type PLA$_2$ in Expressed Sequence Tags (EST) database. Based on the partial sequence, they have found a DNA sequence encoding novel secretory type PLA$_2$ protein from mouse spleen cDNA library. Further, the inventors have found out a DNA sequence encoding human secretory type PLA$_2$ protein (IIE type) from human spleen cDNA library, to accomplish this invention.

The invention relates to:

(1) A protein which comprises an amino acid sequence from first Asn to 123rd Cys of that shown in SEQ ID No.:30;

(2) The protein as described in above (1) which comprises an amino acid sequence from −19th Met to 123rd Cys of that shown in SEQ ID No.:30;

(3) A protein which comprises the amino acid sequence of above (1) or (2), in which one or more amino acid residues are substituted, deleted, inserted, or added, and has a phospholipase A$_2$ activity;

(4) A DNA which encodes the protein as described in any one of above (1), (2) and (3);

(5) The DNA as described in above (4) which comprises a base sequence from 116th A to 484th C of that shown in SEQ ID No.:29;

(6) The DNA as described in above (5) which comprises a base sequence from 59th A to 484th C of that shown in SEQ ID No.29;

(7) A DNA which hybridizes to the DNA as described in above (5) or (6) under the stringent condition and encodes the protein having a phospholipase A$_2$ activity;

(8) An expression vector which has the DNA as described in any one of above (4) to (7);

(9) A transformant which is obtained by inserting the expression vector as described in above (8) to a host;

(10) The transformant as described in above (9) wherein the host is a mammalian cell line;

(11) A method for producing a protein which comprises a step for culturing the transformant as described in above (9) or (10), and a step of recovering the protein as described in any one of above (1), (2) and (3) from the culture;

(12) An antibody which specifically recognizes the protein as described in any one of above (1), (2) and (3);

(13) A diagnostic agent for secretory type phospholipase A$_2$-related diseases, which comprises the antibody as described in above (12);

(14) An assay kit for secretory type phospholipase A$_2$, which comprises the antibody as described in above (12);

(15) A therapeutic agent for secretory type phospholipase A$_2$-related diseases, which comprises the antibody as described in above (12);

(16) A screening method of a compound specifically inhibiting a secretory type phospholipase A$_2$ activity which uses the protein as described in any one of above (1), (2) and (3); and

(17) A composition for use as a IIE type phospholipase A$_2$ inhibitor containing, as an effective ingredient, a compound of the formula (I):

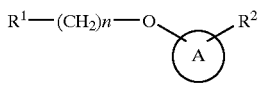

wherein A ring is an optionally substituted carbocycle, or an optionally substituted heterocycle;
$R^1$ is —COOH, —$SO_3H$, or —PO(OH)$_2$;
$R^2$ is —COCONH$_2$, —CH$_2$CONH$_2$, or —CH$_2$CONHNH$_2$;
n is an integer of 0 to 6,
which is obtained by the screening method as described in above (16); and

(18) The composition as described in above (17) wherein the IIE type phospholipase $A_2$ is the protein as described in any one of above (1), (2) and (3).

The protein of this invention is "A protein which comprises an amino acid sequence from first Asn to 123rd Cys of that shown in SEQ ID No.:30". Preferable is "A protein which comprises an amino acid sequence from −20th Met to 123rd Cys of that shown in SEQ ID No.:30". "A protein which comprises an amino acid sequence from first Asn to 123rd Cys of that shown in SEQ ID No.:30" means a mature protein. "A protein which comprises an amino acid sequence from −20th Met to 123rd Cys of that shown in SEQ ID No.:30" is an immature protein that has a signal peptide. The protein of this invention also includes "A protein which comprises the amino acid sequence as described above (1) or (2), in which one or more amino acid residues are substituted, deleted, inserted, or added, and has a secretory type phospholipase $A_2$ activity". Number or site of "substitution, deletion, insertion, addition of amino acid residue" is not limited, if the modified protein has the same activity as the protein consisting of the amino acid sequence shown in SEQ ID No.:30. In this invention, "phospholipase $A_2$ activity" means "phospholipid-cleaving activity that hydrolyzes 2-acyl ester bond of 3-sn-phosphoglyceride in a $Ca^{2+}$-dependent manner".

Although these mutations in the amino acid sequences can be caused naturally by mutation or modification after transcription, artificial modification can also be caused by the DNA of this invention. The protein of this invention includes all proteins which are encoded by modified DNA and have the characteristics as mentioned above regardless of the cause or mean of these modification/mutation.

The DNA of this invention means "a DNA encoding the protein of this invention". As the DNA of this invention, a DNA which encodes the mature protein and comprises a base sequence from 116th A to 484th C of that shown in SEQ ID No.:29 is preferably given for example. More preferably, a DNA which encodes the immature protein and comprises a base sequence from 59th A to 484th C of that shown in SEQ ID No.:29 is given for example. A DNA that hybridizes to the DNA of this invention under the stringent condition and encodes the protein having a secretory type phospholipase $A_2$ activity is also included in the DNA of this invention. "A DNA that hybridizes to the DNA of this invention under the stringent condition" can be obtained by using the DNA of the encoding region as a probe. "Hybridize under the stringent condition" means that positive hybridizing signal can be observed after heating at 42° C. in 6×SSC, 0.5% SDS and 50% formamide solution and washing 68° C. in 0.1×SSC, 0.5% SDS solution.

Using the DNA of this invention, a production of the recombinant protein can be performed based on textbooks and references such as Molecular Cloning etc. More concretely, a transcription initiation codon is added at upper stream of the DNA to be expressed, and a transcription stop codon is added at down stream of the DNA. A regulator gene such as a promoter sequence (Ex. Trp, lac, T7, SV40 initial promoter) which controls transcription is also added. The expression plasmid, which can replicate and work in the host cells, is prepared by insertion of the DNA into an appropriate vector (ex. PBR322, pUC19, pSV.SPORT1 etc.).

The transformant is obtained by insertion of the expression vector into host cells. As a host cell, procaryotes such as E. coli, monocellular eukaryotes such as yeast, and cells derived from multicellular organisms such as insects and mammals are given for examples. Mammal's cells are preferable. As a mammal's cell, CHO cell, 293 cell, COS-7 cell are given for example.

The antibody of this invention is an antibody against the polypeptide of this invention or peptide fragment that can compose the epitope, and includes both of polyclonal antibodies and monoclonal antibodies. Secretory type PLA$_2$ is involved in the release of fatty acids (ex. arachidonic acid). Excess release of fatty acids cause various diseases such as septic shock, adult respiratory distress syndrome, pancreatitis, bronchial asthma, allergic rhinitis, rheumatoid arthritis, etc. It is possible to diagnose these diseases by the evaluation of a concentration of secretory type phospholipase $A_2$. The antibody of this invention provides a diagnostic agent and an assay kit for secretory type phospholipase $A_2$-related diseases. If the antibody inhibits a PLA$_2$ activity, the antibody itself can be a therapeutic agent for the diseases caused by PLA$_2$.

The invention relates to a composition for use as IIE type phospholipase $A_2$ activity inhibitor which containing a compound obtained by the screening method of this invention. The compound has a structural feature shown in following formula (I).

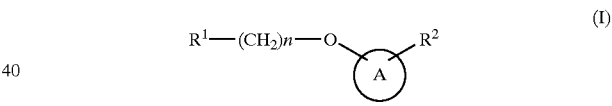

wherein A ring is optionally substituted carbocycle, or optionally substituted heterocycle;
$R^1$ is —COOH, —$SO_3H$, or —PO(OH)$_2$;
$R^2$ is —COCONH$_2$, —CH$_2$CONH$_2$, or —CH$_2$CONHNH$_2$;
n is an integer of 0 to 6.

The term "carbocycle" used in this specification means a ring derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A ring comprising two to three of the carbocycle is also included in the abovementioned ring. An example of the carbocycle includes cycloalkane (such as cyclopropane, cyclobutane, cyclopentane, cyclohexane, cycloheptane, and cyclooctane), cycloalkene (cyclobutene, cyclopentene, cyclohexene, cycloheptene, and cyclooptene), benzene, naphthalene, indene, phenanthrene, anthracene and the like.

The term "heterocycle" used in this specification means a ring derived from monocyclic or polycyclic, saturated or unsaturated, substituted or unsubstituted heterocyclic nucleus having 5 to 14 ring atoms and containing 1 to 3 hetero atoms selected from the group consisting of nitrogen, oxygen and sulfur atom. An example of the heterocycle includes thiophene, thianthrene, furan, pyran, benzofuran, isobenzofuran, chromene, xanthene, phenoxthine, pyrrole, imidazoly, pyrazoly, thiazoly, isothiazoly, oxazoly, isoxazoly, pyridine, pyrazine, pyrimidine, pyridazine, triazine, indolizine, isoindole, indole, indazole, purine, quinolizine, isoquinoline, quinoline, phthalazine, naphthyridine, quinoxaline, quinazoline, cinnoline, pteridine, carbazole, phenanthridine, acridine, perimidine, phenazine, phenothiazine, phenoxazine, pyrrolo [1,2-a] pyrazine, pyrrolo[1,2-b] pyridazine, pyrrolotriazine and the like.

An example of substituents for "optionally substituted carbocycle", "optionally substituted heterocycle" includes alkyl, haloalkyl, alkenyl, alkynyl, carboxy, halogen (F, Cl, Br, I), hydroxyalkyl, hydroxy, nitro, cyano, mercapto, thioformyl, thioacetyl, thiocarboxy, dithiocarboxy, thiocarbamoyl, sulfino, sulfo, sulfamoyl, sulfoamino, optionally substituted aryl, optionally substituted aralkyl, optionally subsituted heteroaryl, optionally substituted heteroarylalkyl and the like. These substituents can be substituted at any one to four arbitrary position of consisting atoms on the above-mentioned carbocycle and heterocycle.

The term "alkyl" means a C1–C8 straight or branched chain alkyl, or aC3–C8 cyclic chain alkyl. An example of the alkyl includes methyl, ethyl, n-propyl, isopropyl, n-butyl, isobutyl, tert-butyl, n-pentyl, isopentyl, n-hexyl, n-heptyl, n-octyl, cyclopropyl, cyclobutyl, cyclopentyl, cyclohexyl, cycloheptyl and the like.

The term "haloalkyl" means a C1–C8 straight or branched chain haloalkyl, or a C3–C8 cyclic chain haloalkyl substituted by at least one halogen. An example of the haloalkyl includes chloromethyl, fluoromethyl, trifluoromethyl, 2,2,2-trifluoroethyl, 1,1-difluoroethyl, trichloromethyl, 2,2,2-trichloroethyl, 1,1-dichloroethyl and the like.

The term "alkenyl" means a C2–C8 straight or branched chain alkenyl, or a C3–C8 cyclic chain alkenyl having at least one double bond. An example of the alkenyl includes vinyl, 1-propenyl, 2-propenyl, isopropenyl, 2-cyclobutentene-1-yl, 2-cyclopentene-1-yl, 3-cyclopentene-1-yl, 2-cyclohexene-1-yl and the like.

The term "alkynyl" means a C2–C8 straight or branched chain alkynyl, or a C3–C8 cyclic chain alkynyl having at least one triple bond. An example of the alkynyl includes ethynyl, 1-propynyl, 2-propynyl, 1-butynyl, 2-butynyl, 3-butynyl and the like.

The term "halogen" leans fluorine, chlorine, bromine and iodine.

The term "aryl" means a C6–C14 aromatic mono ring or aromatic condensed ring. An example of the aryl includes phenyl, naphthyl (such as 1-naphthyl, 2-naphthyl), anthryl (suchas 1-anthryl, 2-anthryl, 3-anthryl) and the like.

The term "aralkyl" means a group wherein the aforementioned "alkyl" is substituted with the above-mentioned "aryl". Such aryl may have a bond at any substitutable position. An example of the aralkyl includes benzyl, phenylethyl (such as 2-phenylmethyl), phenylpropyl (such as 3-phenylpropyl), naphthylethyl (such as 1-naphthylethyl, 2-naphthylethyl), anthrylmethyl (such as 9-anthrylmethyl) and the like. Particulary, benzyl and phenylethyl are preferred.

The term "heteoaryl" means a 5 to 6 membered aromatic ring which contains one or more hetero atoms selected from the group consisting of oxygen, sulfur and nitrogen atoms.

The term "heteroarylalkyl" includes a group wherein the aforementioned "alkyl" is substituted with the above-mentioned "heteroaryl". Such heteroaryl may have a bond at any substitutable position. An example of the heteroarylalkyl includes thienylmethyl (such as 2-thienylmethyl), thienylethyl (such as 2-(thiophene-2-yl)ethyl), furylmethyl (2-furylmethyl), furylethyl (such as 2-(furan-2-yl)ethyl), pyrrolylmethyl (such as 2-pyrrolylmethyl), pyrrolylethyl (such as 2-pyrrole-2-yl)ethyl), imidazolylmethyl (such as 2-imidazolylmethyl, 4-imidazolylmethyl), imidazolylethyl (such as 2-(imidazole-2-yl)ethyl), pyrazolylmethyl (such as 3-pyrazolylmethyl), pyrazolylethyl (such as 2-(pyrazole-3-yl)ethyl), thiazolylmethyl (such as 2-thiazolylmethyl), thiazolylethyl (such as 2-(thiazole-2-yl)ethyl), isothiazolylmethyl(such as 3-isothiazolylmethyl), isoxazolylmethyl (such as 3-isoxazolylmethyl), oxazolylmethyl (such as 2-oxazolylmethyl), oxazolylethyl (such as 2-(oxazole-2-yl)ethyl), pyridylmethyl (such as 2-pyridylmethyl, 3-pyridylmethyl, 4-pyridylmethyl), pyridylethyl (such as 2-pyridylethyl) and the like.

An example of substituents for "optionally substituted heteroaryl" and "optionally substituted heteroarylalkyl" includes alkyl, haloalkyl, alkenyl, alkynyl, carboxy, halogen (F, Cl, Br, I), hydroxyalkyl, hydroxy, nitro, cyano, mercapto, thioformyl, thioacetyl, thiocarboxy, dithiocarboxy, thiocarbamoyl, sulfino, sulfo, sulfamoyl, sulfoamino and the like.

BEST MODE FOR CARRYING OUT THE INVENTION

Figure 1:
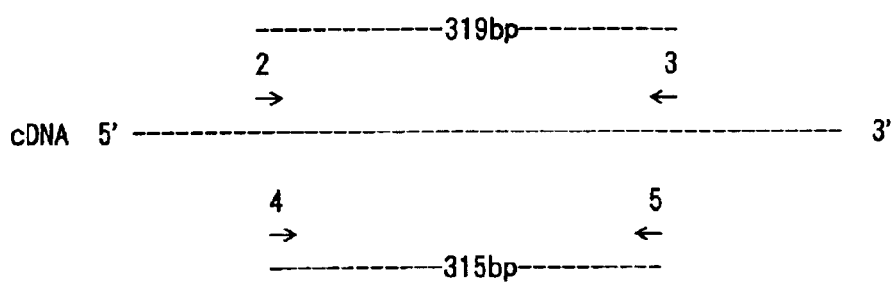
FIG. 1 shows a positional relationship of oligomers of SEQ ID No.:2, 3, 4, and 5.

This invention mainly relates to a novel human secretory type phospholipse $A_2$.

Explained below are a preparation method for the protein of this invention, a preparation method for the antibody, and a screening method for the compound which inhibits the phospholipase $A_2$ activity as below. Unless otherwise mentioned, for example, gene recombinant, production methods for a recombinant protein using animal cells, insect cells, yeast and *E. coli*, separation and purification methods for the expressed protein, analysis method, immunological means, technologies well-known in this field, can be used to this invention.

The DNA Sequence Encoding the Secretory Yype $PLA_2$ of this Invention

The DNA of this invention can be produced or obtained based on the sequence information described in this invention by general gene engineering-technique (Molecular Cloning 2d Ed, Cold Spring Harbor Lab. Press (1989) so on). More specifically, cDNA library is prepared by conventional methods from appropriate sources expressing the DNA of this invention, and the DNA clone is selected from the library using specific probes or antibodies (Proc. Natl.

Acad. Sci., USA., 78, 6613 (1981); Science, 22, 778 (1983) so on). Examples of the cDNA source are cells and tissues that express the DNA of this invention or cultured cells derived from these cells or tissues. Separation of total RNA, separation and purification of mRNA, obtaining cDNA and it's cloning can be performed by conventional methods. The commercially available cDNA libraries such as Clontech library can also be used.

The screening method for the DNA of this invention from the library is not limited, and can be performed by conventional methods. Available methods are as follows: an immunological screening for the corresponding cDNA clone using a specific antibody for the protein encoded by the cDNA, a plaque hybridization using a probe that selectively binds to the objective DNA, a colony hybridization and so on and combination of these methods. DNA Probes used in these methods are chemically synthesized based on the information of the DNA sequence or a fragment of the obtained DNA of this invention. Also sense/antisense primers designed from the information of the sequence can be used for cloning probes.

DNA/RNA amplification by PCR method (Science, 230, 1350 (1985)) can suitably be used for obtaining the DNA of this invention. If it is difficult to obtain the full length cDNA from the library, various methods such as RACE (Rapid amplification of cDNA ends;: Experimental Medicine, 12(6), 35 (1988)) can be supplemented. The primers used for the PCR method can be designed based on the sequence information of the DNA clarified by this invention. Such primers can be synthesized by conventional methods. Isolation and purification of the amplified DNA/RNA fragments can also be performed with conventional method descried above. For example, it can be performed by gel electrophoresis etc. The DNA or various fragments obtained at the above methods can be sequenced by dideoxy method (Proc. Natl. Acad. Sci., USA., 74, 5463 (1977)), Maxam and Gilbert method (Methods in Enzymology, 65, 499 (1980)) or by using a sequencing kit etc.

Hereafter, the DNA cloning method of this invention is described. (1) Sequence determination of the DNA encoding the mouse secretory type $PLA_2$ A sequence determination method for the DNA fragment encoding mouse secretory type $PLA_2$ which corresponds to human secretory type PLA2 of this invention is described below. Finding out a sequence homologous to mouse X type PLA2 is firstly done. Next step is preparing primers on the basis of the sequence. And finally, PCR is performed using cDNA library originated mouse spleen as a template. By sequencing the obtained DNA fragment, the DNA fragment encoding mouse secretory type $PLA_2$ can be determined.
(A) Isolation of a Novel $PLA_2$ cDNA Fragment and Analysis of Expression Pattern in Mouse Tissues In order to analyze the gene from which a DNA fragment is originated and function of a protein encoded by the gene, it is necessary to isolate cDNAs which connect to 5' terminus and 3' terminus of this fragment and to confirm the sequence integrity. For this purpose, it is advantageous to use tissues with high expression level of the gene.

The existence of the expression and its level among tissues can be analyzed by a hybridization with radio-labeled DNA fragment (probe) with mRNAs extracted from each tissue immobilized on a sheet (Northern hybridization). It is necessary to obtain a $PLA_2$ cDNA fragment used as a probe for comparing the quantities in mouse tissues. Such a fragment can be isolated by PCR using primers prepared based on the sequence of EST database and using a cDNA sample originated from mouse tissues as a template. The northern analysis was performed by the obtained cDNA fragment (SEQ ID No.:1). The result indicated clearly that the gene is highly expressed in mouse heart.
(B) Isolation of Full Length cDNA Encoding Mouse Secretory Type $PLA_2$ For example, upper stream sequence including 5' terminus of the cDNA and down stream sequence including 3' terminus of the cDNA can be obtained by PCR with so called RACE method: Rapid Amplification of cDNA End. Oligomer pairs used in the PCR consist of one $PLA_2$-specific primer, and the other that corresponds to adapter sequence which is added on the 5' and 3' end of the cDNA. Marathon-ready cDNA (Clontech) originated mouse spleen can be used as a cDNA sample. DNA sequence having mouse secretory type $PLA_2$ gene and the amino acids sequence encoded by the gene obtained by the method are shown in SEQ ID No.:14 and 15, respectively.
(C) Isolation of Full Length cDNA Encoding Human Secretory Type $PLA_2$ Generally, it is expected that the same gene have high sequence homology between mouse and human. It is expected that the amino acids residues conserved in $PLA_2$s originated from various animals (consensus sequence) of which primary structure has been determined are also conserved in the novel $PLA_2$. Therefore, the cDNA sequence corresponding to the consensus sequence would have high homology with cDNA of human type $PLA_2$ and this region will be useful for the cloning of human homolog based on the mouse $PLA_2$ sequence information. Furthermore, the mouse cDNA sequence of this invention has high homology with IIA, IID type. It can be predicted that the human secretory type $PLA_2$ gene of this invention also has high homology with IIA, IID type. Based on the above assumption, the oligomers were designed by the consensus sequence conserved in these $PLA_2$ and partial sequence corresponding to human secretory type $PLA_2$ was cloned by PCR using human genomic DNA (Boehringer Mannheim) as a template. For example, upper stream sequence including 5' terminus of the cDNA and down stream sequence including 3' terminus of the cDNA can be obtained by PCR with RACE method described above. The oligomer pairs used in the PCR consist of one $PLA_2$-specific primer, and the other corresponds to adapter sequence which is added on the 5' and 3' end of the cDNA. Or it can be obtained by PCR using human cDNA library as a template based on mouse $PLA_2$ cDNA sequence which can be expected to have high homology with human counterpart. Marathon-ready cDNA of human small intestine which is expected to express highly was used as a template. DNA sequence having human secretory type $PLA_2$ gene and the amino acids sequence encoded by the gene obtained by the method are shown in SEQ ID No.:29 and 30, respectively.

Preparation of the Protein of this Invention
(1)Expression of a Recombinant Type $PLA_2$ Protein The protein of this invention can be obtained as a recombinant protein by genetic engineering means (Science, 224, 1431 (1984); Biochem. Biophys. Res. Comm., 130, 692 (1985); Proc. Natl. Acad. Sci., USA., 80, 5990 (1983) etc.). More specifically, a gene encoding a desired protein is inserted into an appropriate vector. A transformant is obtained by incorporating the vector into host cells. A recombinant protein can be obtained by the culture of the transformant.

Both eucaryote and procaryote can be used as host cells. The eucaryote's cells include cells of vertebrate and yeast etc. COS cell (Cell, 23, 175 (1981)) of ape and ovarian cell of a Chinese hamster so on are used as the vertebrate cells.

An expression vector which has a promoter located in upper stream of the gene aimed for expression, splice junction of RNA, polyadenylation region and transcription end sequence so on can be used. And the vector may have a replication origin if it is necessary. As an example for the expression vector is pSV2dhfr (Mol. Cell. Biol., 1, 854 (1981)) having SV40 early promoter etc. As a eucaryotic microorganism, yeast, especially Saccharomyces yeast, is widely used. pAN82(Proc. Natl. Acad. Sci., USA., 80, 1 (1983)) having promoter for acid phosphatase gene etc. can be used as the expression vector for yeast.

As a host of a procaryote, E.coli or Bacillus subtilis are widely used. If these cells are used as a host, it is preferable to use plasmid vector which is replicable in the host and contains a promoter for expression of an objective gene at upper stream of the gene, SD sequence, initiation codon necessary for starting protein synthesis. As a host, E. coli K12 strain etc. is used. As a vector, generally pBR322 and it's derivative are used. It is not limited to these host/vector system. Various kinds of known strains and vectors can also be used. As a promoter, trp promoter, 1pp promoter, lac promoter, PL/PR promoter, etc. can be used.

As an insertion method of a desired recombinant DNA into host cell and a transformation method, various general methods are employable. The obtained transformant can be cultured according to general methods and the desired protein can be produced by the culture. As a medium used for the culture, appropriate medium can be selected from various kinds of commonly used medium according to a host cells. For example, the transformant can be prepared by an insertion of the vector comprising human secretory type $PLA_2$ gene of this invention at down stream of PSVL SV late promoter and the recombinant secretory type $PLA_2$ protein can be produced by a culture of the transformant at 37° C. for 3 days under the existence of 5% $CO_2$.

The recombinant protein can be separated and purified by various separating procedures utilizing its physical and chemical characteristics, etc. (Biochemistry, 25(25), 8274 (1986); Eur. J. Biochem., 163, 313 (1987) etc.). For such separating method, extraction by salt, centrifugation, osmotic shock method, ultrasonication, ultrafiltration, gel filtration, various kinds of liquid chromatography such as adsorption chromatography, ion exchange chromatography, affinity chromatography, or high performance liquid chromatography, dialysis, and combination of these method are applicable examples.

(2) Preparation of Variant

Amino acid sequence can be changed with deletion/insertion at any position. The methods known as protein engineering can be widely applicable to the substitution of the amino acids sequence. Site-directed deletion method (Nucl. Acids Res., 11, 1645, (1983)), Site-specific mutagenesis method (Zoller, M. J. et al., Methods in Enzymol., 100, 468, (1983), Kunkel. T. A. et al., Methods in Enzymol., 154, 367–382, (1987)), PCR mutation method, method using restriction enzyme and synthesized gene, etc. are the applicable examples.

Using site-specific mutagenesis inducing method described in Sambrook, J. et al., Molecular Cloning: A Laboratory Manual 2nd, No.1–3, Cold Spring Harbor Laboratory Press publication New York (1989) or PCR method as a Site-specific mutagenesis method, mutations can be introduced into the DNA sequence of this invention.

By using appropriate vector and host strain, the DNA sequence mutated by these methods can be expressed with genetic engineering method described such as in Sambrook, J. et al., Molecular Cloning: A Laboratory Manual 2nd, No.1–3, Cold Spring Harber Laboratory Press publication New York (1989). Several kits such as Mutan™-SuperExpress Km Mutan™-K (Takara shuzo), Quick Change Site-Directed Mutagenesis Kit (Stratagene) can be used.

Generally, site-specific mutagenesis method can be performed by obtaining a single strand vector including the sequence encoding the protein. Oligo nucleotide primer with desired mutation in the sequence can be produced by general synthesis method, such as Crea's method (Crea, R. et al., Proc. Natl. Acsd. Sci. U.S.A., 75, 5765, 1978). Annealing of this primer with the single strand vector having this DNA sequence is performed, then reaction with DNA polymerase such as E. coli polymerase I Klenow flagment is followed to complete the synthesis of the mutated strand. Hetero double strands comprising one strand encoding non-mutation sequence and another strand having desired mutation are formed. Appropriate bacteria or cells are transformed by this double strand vector. The clone is selected by hybridization of radioactivity probe consisted of $^{32}P$-labeled mutated sequence-including primer (Wallace, R. B., Nucleic Acids Res., 9, 3647, 1981). Selected clone contains the recombinant vector having mutated sequence. After the selection of such clone, the region encoding mutated protein can be inserted into an expression vector for transformation.

Hereafter, variants can be produced by the host cells according to the preparation method of the recombinant protein shown in (1).

Determination of Secretory Type PLA, Activities

The determination of $PLA_2$ activities of the recombinants and the variants obtained above was carried out by the following method.

① React the culture products containing recombinant secretory type $PLA_2$ protein or the control culture products containing no recombinant secretory type $PLA_2$ protein with $^3H$-oleic acid-labeled E. coli membrane phospholipid fractions.

② Determine the quantity of released $^3H$-oleic acid according to Elsbach's method (Methods Enzymol., 197, 24–31 (1991)).

③ Certify the existence of $PLA_2$ activity by comparing the quantity of $^3H$-oleic acid.

Preparation of Antibody Against the Protein of this Invention

The antibody against the protein of this invention can be produced by the following methods.
(1) Preparation of Polyclonal Antibody Peptides synthesized by a usual peptide synthesizer based on a part of the deduced amino acids sequence are used as immunogen. Alternatively, protein produced by bacteria, yeast, insect cells and mammalian cells, which are transformed by the expressing vector encoding the protein into, can be purified by general protein chemical method and also used as immunogen. Thus, the polyclonal antibody that specifically recognizes the protein can be easily prepared and purified. Using this immunogen, animals are immunized according to the appropriate method described in Antibodies; A Laboratory Manual, Lane, H. D. et al., Cold Spring Harber Laboratory Press publication New York 1989. For example, polyclonal antibody is prepared from the serum of the immunized animals, such as mouse, rat, hamster, and rabbit.
(2) Monoclonal Antibody Lymphocytes are isolated from spleen or lymph node of the immunized mouse or rat with the immunogen as described above. Hybridomas are prepared by fusion of the isolated lymphocyte and myeloma cells according to Kohler and Milstein's method (Nature, 256, 495–497(1975)). Monoclonal antibody can be produced from the hybridoma. For example, the monoclonal antibody against the protein of this invention can be obtained by the following steps:

(a) Immunization of mice by the protein, (b) Isolation of immunized mouse spleen and separation of the spleen cells, (c) Fusion of separated spleen cells and mouse myeloma cells in the presence of fusion-promoting agent, such as polyethylene glycol, according to Kohler's method described above, (d) Culture of hybridoma cells obtained from selective medium in which unfused myeloma cells can not grow, (e) Selection of hybridoma cells that produce the desired antibody by the evaluation with enzyme-linked immunosorbent assay (ELISA), and western blot, and cloning them by the limited-dilution method etc., (f) Culture of the hybridoma cells that produce the monoclonal antibody and collection of the monoclonal antibody.

Assay Kit for Secretory Type $PLA_2$, and Diagnostic Reagent for Secretory Type $PLA_2$, Relating Disease In this invention, the protein of this invention can be assayed by using the monoclonal antibody against the protein. Any kind of assay using the antibody against the protein of this invention is applicable, if the assay determines the quantity of antibody corresponding to the antigen quantity (ex. Quantity of the protein of this invention) in the assay solution, or the quantity of antibody-antigen complex by the chemical or physical methods, and calculates them by the standard curve prepared by using the standard solution containing a known quantity of the antigen. For examples, nephelometry, competition method, immunometric assay, and sandwich method can be adapted.

For the immobilization of the antigen or the antibody, the chemical binding generally useful for immobilization of the protein or enzyme can be used. As a carrier, insoluble polysaccharides such as agarose, dextran, or cellulose, or synthetic resins such as polystyrene, polyacrylamide, silicon, or glass are given for examples.

In the sandwich method, the quantity of the protein in assay solution can be determined by the following steps.

(1) React the immobilized antibody of this invention with the assay solution, then react them with another labeled-antibody of this invention.

(2) Determine the activity of the labeling agent on the immobilized carrier.

There is no need that the immobilized antibody is the same as the labeled antibody. For example, if the immobilized antibody recognizes the N-terminus of the protein, the labeled-antibody that recognizes C-terminus of the protein can be used.

Radioisotope, enzyme, and fluorescent substance can be used as a labeling agent. As a radioisotope, $^{125}I$, $^{3}IH$, $^{14}C$ etc. can be used. As an enzyme, peroxydase, β-galactosidase, β-glucosidase, alkaline phosphatase, etc., can be used.

By using these assay, if the concentration of the protein is excess, it is possible to diagnose or diagnose patients with the diseases such as septic shock, adult respiratory distress syndrome, pancreatitis, external injuries, bronchial asthma, allergic rhinitis, rheumatoid arthritis, etc.

Therefore, the antibody of this invention provides "Diagnostic reagent" and "Assay kit" which can be useful in the diagnosis of these diseases.

Screening Method for a Compound that Specifically Inhibits $PLA_2$, Activity

As a "Screening method" of this invention, high through put screening with the protein of this invention is given for example. For example, samples, phospholipid substrate (racemic diheptanoyl thio-phosphatidylcholine) and color-developing reagent (5,5'-dithiobis (2-nitrobenzoic acid)) are added into 96-well plate according to the Reynolds's method (Anal. Biochem. 204, 190–197(1992)). After the addition of the protein, the wells were incubated at 40° C. for the appropriate time, and the change of absorbance (OD at 405 nm) is measured. The inhibiting activity of the sample for this secretory type $PLA_2$ can be evaluated by comparing with the value obtained in the absence of the sample.

Compound Obtained from the Screening Method

Secretory type $PLA_2$ is involved in the release of fatty acids (ex. arachidonic acid). Excess release of fatty acid causes various diseases such as septic shock, adult respiratory distress syndrome, pancreatitis, external injuries, bronchial asthma, allergic rhinitis, rheumatoid arthritis. The compound obtained from the screening method inhibits the activity of secretory type $PLA_2$. Therefore, the compound is useful for the therapy of diseases including septic shock in which the excess production of secretory type $PLA_2$ is involved.

The compound includes pharmaceutically acceptable salts. The salt is prepared by well-known methods. Non-toxicity alkaline metal salt, such as sodium, potassium, litium, calcium, magnesium, and barium, alkali earth metal salt, and ammonium salt, etc. are included.

A pharmaceutical preparation is made with a pharmacologically effective quantity of the compound as an active ingredient. As a medication unit form of the pharmaceutical preparation, various kinds of form can be selected according to an object of therapy. As a solid dosage form, tablet, pill, powder, epipastic, granule, capsule, etc. are included. And as a liquid dosage form, solution, suspension, emulsion, syrupus, elixir, etc. are included. These are classified into oral agent, non-oral agent, nasal agent, vaginal agent, suppository, sublingual agent, ointment, etc. according to the dosage route. Preparation and molding can be performed according to the general methods.

The dosage forms of the pharmaceutical preparation as described above are not limited and these are determined according to each preparation form, age of subjects, sex, state of a disease or other condition. For example, tablet, pill, granule, capsule, solution, suspension, and emulsion are given through oral. An injection agent is used by itself or as the mixture with a general fluid replacement such as dextrose or amino acids, and given through vein. Moreover, injection is given into muscle, skin, abdominal cavity or under skin, if necessary.

The effective quantity of the invention compound should be comprised in the pharmaceutical preparation as mentioned above and its dosage is not limited. It is chosen according to the effect of desired therapy, the dosage method, the duration of therapy, the age of subject, sex, and the other conditions. Generally, the dosage is about 1–10 mg per 1 kg body weight a day. The preparations can be given in one to several divisions per day.

The antibody of this invention inhibits the $PLA_2$ activity of the secretory type $PLA_2$ of this invention via the specific binding to PLA2 of this invention. Therefore, the antibody of this invention, as well as the compound obtained from the screening method of this invention, are useful for the therapy of diseases, such as septic shock, in which excess production of secretory type $PLA_2$ is involved.

EXAMPLE

The invention is explained in more detail by the following examples.

General experiment protocols used in each step in this invention follow Current Protocols in Microcular Biology (F. M. Ausubel et al. Ed., John Wiley & Sons. Inc.). DNA oligomers were purchased from International Reagents Corp. (Kobe, Japan). Data analysis was performed with GENETYX-SV/RC of Software Development Inc. (Japan). Determination of DNA sequences was routinely performed with several clones in order to eliminate the effects of misincorporation that might be caused in the PCR reactions.

cDNA fragment that can encode the $PLA_2$ detected in EST database is shown as SEQ ID No.:1 at Sequence Listing. This sequence is a fragment. It is required to isolate the undetected cDNAs connected with 5' terminus and 3' terminus of the fragment and to reconfirm the fragment sequence at the same time for the analysis of the fragment-originated gene itself and the function of the protein encoded by the gene. For the cloning the full length cDNA, it is favorable to use the tissues in which the gene is highly expressed. In order to compare the quantities of the gene expression levels among the mouse tissues by Northern analysis, it is required to obtain a $PLA_2$ cDNA fragment available for the probe. Such $PLA_2$ cDNA fragment can be isolated by PCR using cDNA samples derived from mouse tissues as templates.

Example 1

Isolation of a cDNA fragment of a novel mouse $PLA_2$

Short DNA oligomers shown in SEQ ID No.:2 to 5 were prepared based on the DNA sequence shown in SEQ ID No.:1. A relative positioning of these DNA oligomers are shown in FIG. 1. 319 base pairs of $PLA_2$ cDNA fragments could be amplified by PCR using the oligomer pair of SEQ ID No.:2 and 3, and 315 base pairs of $PLA_2$ cDNA fragments could be amplified by PCR using oligomers of the SEQ ID No.:4 and 5. If PCR was performed by using oligomers of SEQ ID No.2 and 3 at first, then amplified products were used as templates at second PCR with oligomers of SEQ ID No.4 and 5, it was expected that $PLA_2$ cDNA could be amplified with higher specificity and sensitivity (Nested-PCR).

cDNA samples were prepared from reverse transcription of mRNA extracted from mouse tissues (brain, heart, kidney, spleen, stomach, etc.) of 129/Svj strain. Using these cDNA samples as templates, PCR was performed using oligomers of SEQ ID No.:2 and 3. TaKaRa Ex Taq (Takara Shuzo, Japan) was used as an enzyme, and composition for PCR reaction was followed to the instruction of the enzyme. As an amplification device, Thermal Cycler (Perkin Elmer Cetus) was used. The amplification was performed at 94° C. for 1 min, 55° C. for 1 min, and 72° C. for 1 min for 30 cycles. After the reaction was completed, second PCR was performed using 1 µl of the reaction solution as template with oligomers of SEQ ID No.:4 and 5. The reaction condition was same as the first PCR. The solution of the PCR reaction was applied to 1.2% agarose gel electrophoresis and the amplified products were separated. The DNA of the expected size was amplified from the cDNA originated with all tissues.

The DNA was cut out from the gel. Purification of DNA was performed using GenElute Agarose spin column (Spelco). The DNA was ligated with pCRII vector (Invitrogen), and *E. coli* DH 5α strain (Toyobo) was transformed with the ligation solution. The obtained recombinant *E. coli* was cultured, and plasmid DNA was prepared by GFX Micro Plasmid Prep Kit (Pharmacia Biotech). The sequence inserted into the vector was determined with PRISM 310 Genetic Analyzer (PE Applied Biosystems). The result indicated that the DNA consisted of the sequence corresponding to SEQ ID No.:1 was amplified by the PCR.

Example 2

Analysis of Expression Pattern of the Secretory Type $PLA_2$ mRNA in Each Mouse Tissue The existence and its level of the expression in tissues can be analyzed by a hybridization with radio-labeled DNA fragment (probe) with mRNAs extracted from each tissue immobilized on a sheet (Northern hybridization). The purified DNA fragment after the PCR amplification was labeled with Megaprime DNA labling sysytem (Amersham Pharmacia Biotech). Using this fragment as a probe, the hybridization was performed with mouse Multiple tissue northern blot (Clontech). Autoradiography was performed after the washing with the solution containing appropriate concentration of salt. The result indicated that the $PLA_2$ mRNA was highly expressed in heart among the tissues examined.

Example 3

Determination of cDNA primary construction of mouse secretory type $PLA_2$

Up stream including 5' terminus and down stream including 3' terminus of the cDNA can be isolated by the following method utilizing the information of known portion (central part) of the cDNA. Several antisense oligomers and sense oligomers are prepared according to the known sequence. cDNA including unidentified part can be amplified using cDNA samples which has attached adapter DNAs at the end of cDNA. Oligomer pairs consisted of a oligomer corresponding to the adapter-specific sequence and a $PLA_2$ specific oligomer are used (RACE method).

Mouse spleen Marathon-ready cDNA (Clontech) was used as a cDNA sample. Oligomers used for the RACE method were shown in SEQ ID NO.:6 to 9. Among them, SEQ ID No.:6 and 7 are antisense oligomers for isolating 5' up stream, and SEQ ID No.:8 and 9 are sense oligomers for isolating down stream.

RACE method was performed by Nested PCR as same as PCR amplification of the central portion. For 5' side RACE, the oligomer of SEQ ID No.:6 and oligomer AP-1 attached with RACE kit (Clontech) were used at the first RACE, and the oligomer of SEQ ID No.:7 and oligomer AP-2 (Clontech) were used at the second RACE. For 3' side RACE, the oligomer of SEQ ID No.:8 and AP-1 were used at the first RACE, and the oligomer of SEQ ID No.:9 and AP-2 were used at the second RACE. TaKaRa Ex Taq (Takara Shuzo, Japan) was used as an enzyme. The first amplification was performed at 94° C. for 1 min, 60° C. for 1 min, and 72° C. for 2 min for 30 cycles, the second amplification was performed at 94° C., for 1 min, 62° C. for 1 min, and 72° C. for 2 min for 30 cycles. After the PCR, the amplified products were separated by electrophoresis. A band of about 450 base pair was detected by 5'RACE and a band about 470 base pair was also detected by 3' RACE. The cloning of these DNAs were performed as the same way of Example 1 and the sequences were determined by PRISM 310 Genetic Analyzer (PE Applied biosystems).

Three parts of PLA$_2$ cDNA were isolated separately. Those are upper region, central part, and down-stream region. To confirm that these cDNAs are derived from one integral gene, oligomers shown at from SEQ ID NO.:10 to 13 were prepared and the PCR was performed using Marathon-ready cDNA (Mouse spleen, Clontech) as a template with oligomers shown at SEQ ID NO.:10 and 12. The second PCR was performed using 1 μl of the reaction solution as template with oligomers of SEQ ID No.:11 and 13 after the reaction. TaKaRa Ex Taq (Takara) was used as an enzyme for the each PCR. The amplification was performed at 94° C. for 1 min, 60° C. for 1 min, 72° C. for 4 min for 30 cycles. The amplified DNA was cloned as same as described above, and the sequence was determined. The determined cDNA sequence is shown at SEQ ID No.:14 and the amino acids sequence encoded by the cDNA is shown at SEQ ID No.:15.

From the length of the cDNA encoding the protein, it is clear that the number of amino acid residues of the PLA$_2$ protein is 142. This protein possesses all structural features (central part for PLA$_2$ activity, sequence of Ca$^{2+}$ binding part, number of Cys residues) conserved among the secretory type PLA$_2$ family molecules. However, this protein consists of a different sequence from any of known secretory type PLA$_2$s, and homology at the amino acids level are 35.8% with mouse IB type, 47.7% with mouse IIA type, 38.0% with mouse IIC type, 41.8% with mouse IID type, 41.0% with mouse V type, and 35.8% with mouse X Type, respectively.

Example 4

Determination of cDNA Primary Construction of Human Secretory Type PLA$_2$

Generally, it can be expected that the same type gene of mouse and human have high sequence homology each other. It was considered that the cDNA sequence corresponding to the consensus sequence in mouse cDNA sequence would have high homology to human PLA$_2$ and this region is useful for the cloning of human homolog based on the mouse PLA$_2$ gene information. It was proved that the mouse cDNA sequence determined at Example 3 has high homology to IIA type and IID type. Therefore, it was expected that the human secretory type PLA2 gene corresponding to the mouse PLA$_2$ gene would have high homology to human IIA type and human IID type. Two oligomers were designed on basis of the mouse cDNA sequence, consensus sequence of human IIA type and human IID type.

An oligomer (Sense oligomer) of SEQ ID No.:16 was prepared on the basis of cDNA sequences corresponding to 23rd Tyr to 28th Gly shown in SEQ ID No.:14 with the consideration of cDNAs corresponding to human IIA type and human IID type. And other oligomer (Antisense oligomer) of SEQ ID No.:17 were also prepared on the basis of cDNA sequence corresponding to 46th His to 52nd Arg shown in SEQ ID No.:14. The IIA type like human PLA$_2$ gene including IIA type was isolated with high sensitivity and high specificity by PCR using these oligomers from human Genomic DNA. Using Human Genomic DNA of Boehringer Mannheim as templates, PCR was performed at 94° C. for 1 min, at 50° C. for 1 min, at 72° C. for 2 min for 30 cycles and the other condition was as same as Example 1. Three types-amplified products consisting of about 800, 350, and 300 base pairs were detected after the electrophoresis.

These fragments were cloned as same as Example 1 and the sequence of the fragments were determined. From the results, it became clear that the DNA fragment of about 800 base pairs is human IIA type PLA2 and the DNA fragment of about 350 base pairs is human IID type PLA2. These fragments have an intron sequence at the same position. Therefore, it was expected that novel PLA$_2$ would have an intron at the same position. The DNA fragment of about 300 base pairs is shown in SEQ ID No.:18. This base sequence contains a 212 base pairs sequence (from 58$^{th}$ to 269$^{th}$ of SEQ ID no.:18) expected to be an intron at the same position of IIA type and IID type. Homology of the sequence expected to be an exon is 85.1% with the corresponding mouse cDNA region determined at Example 3. Thus, it can be expected that this fragment is a part of a novel human PLA$_2$ gene.

Based on the obtained base sequence, three sense oligomers and three antisense oligomers were designed. These oligomers are shown in SEQ ID No.:19 to 24.

For detecting tissues with high expression level of the gene, Nested-PCR was performed as the same way of Example 1 by using these oligomers and human cDNA originated from various tissues as templates. First PCR was performed by using oligomers of SEQ ID No.:19 and 22. Second PCR was performed by using the amplified products as template with oligomers of SEQ ID No.:20 and 23. Both the first and the second PCR were performed at 94° C. for 1 min, at 55° C. for 1 min, at 72° C. for 1 min for 30 cycles and the other condition was as same as Example 1. Maraqthon-ready cDNA (Human kidney, pancreas, small intestine, spleen, lung, heart, leukocyte, liver) were used as templates. From the result, it was expected that small intestine is a tissue with high expression level of the gene. The obtained fragment was cloned as same as Example 1 and the base sequence was determined. From the result, it became clear that the cDNA sequence consist of the expected exon region.

The upper stream including 5' terminus was isolated by RACE method. The experiment was conducted on the condition described in Example 3 and Marathon-ready PCR cDNA (Human spleen, Clontech) was used as a template. SEQ ID No.:23 and 24 were used for antisense oligomer for isolating upper stream. After the RACE, DNA fragments of about 120 base pairs was obtained and the sequence was determined. Two antisense oligomers (SEQ ID No.:25 and 26) were designed for isolating further upper stream and RACE was performed as the same way. After the RACE, DNA fragment of about 150 base pairs was obtained and the sequence was determined.

The down stream including 3' terminus was isolated by the following Nested-PCR. It has become clear that the homology of novel human PLA2 is very high with the corresponding mouse PLA2 from the obtained base sequence. Based on the mouse cDNA sequence (SEQ ID No.:14) determined Example 3, two antisense oligomers (SEQ ID No.:27 and 28) corresponding to 595th–615th and 601st–621st of the sequence were prepared. PCR was performed by using these oligomers as antisense primers. First PCR was performed by using oligomers of SEQ ID No.:20 and 28. Second PCR was performed by using the amplified products as template with oligomers of SEQ ID No.:21 and 27. Both the first and the second PCR were performed at 94° C. for 1 min, at 55° C. for 1 min, at 72° C. for 2 min for 30 cycles and the other condition was as same as Example 1. Maraqthon-ready cDNA (Human small intestine, Clontech) was used as a template. From the PCR, DNA fragment of about 300 base pairs was obtained and the base sequence was determined as same as Example 1.

The central part, the two upper streams, and the two down streams of the $PLA_2$ cDNA were partially isolated at the above steps. These sequences have continuity and the connected sequence is shown at SEQ ID No.:29.

From the length of the cDNA encoding the protein, the number of amino acid residues of the $PLA_2$ protein is 142. This protein (SEQ ID No.:30) conserves all structural features (central part of $PLA_2$ activity, sequence for $Ca^{2+}$ binding part, and number of Cys residues) conserved among secretory type $PLA_2$ family molecules. However, this protein consists of a different sequence from any of known secretory type $PLA_2$s, and homology of the amino acids sequence is 39.0% with human IB type, 51.4% with human IIA type, 39.2% with human IID type, 45.7% with human V type, and 38.2% with human X type.

Example 5

Expression of the Recombinant $PLA_2$ Protein

Nested-PCR was performed by using the oligomers(SEQ ID No.:31–34) which were prepared on the basis of the obtained cDNA sequence, and the cDNA sequence encoding the region of the amino acids (the cording region) was amplified. SEQ ID No. 31 and 33 were used for the first PCR. SEQ ID No.:32 and 34 were used for the second PCR. Marathon-ready PCR cDNA (Human Small Intestine) of Clonthech was used as a template. The oligomer shown in SEQ ID No.:32 has a sequence recognized by the restriction enzyme NotI and a sequence (Kozak sequence) that promotes the transcription from mRNA to protein. The oligomers shown in SEQ ID No.:34 has a sequence recognized by the restriction enzyme XbaI. There is no sequence recognized by the restriction enzyme NotI or XbaI within the cording region. Therefore, after the digestion of PCR-amplified cDNA fragments with these restriction enzymes, the cDNA corresponding to the cording region can be prepared. It has the Kozak sequence at upper stream of the transcription starting point and the cutting edges of NotI or XbaI on the upper terminus and the down stream terminus of the cDNA, respectively.

Figure 2:
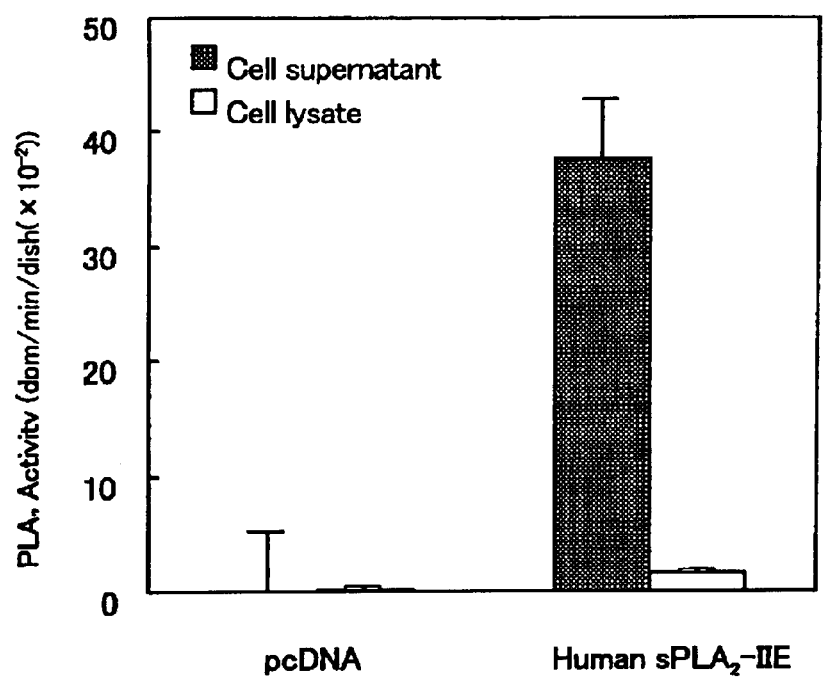
FIG. 2 shows the $PLA_2$ activities of the Lysate and Supernatant of the transformants. One of the transformants has the gene encoding human secretory type $PLA_2$ of this invention. The other transformant does not have the $PLA_2$ gene.
Figure 3:
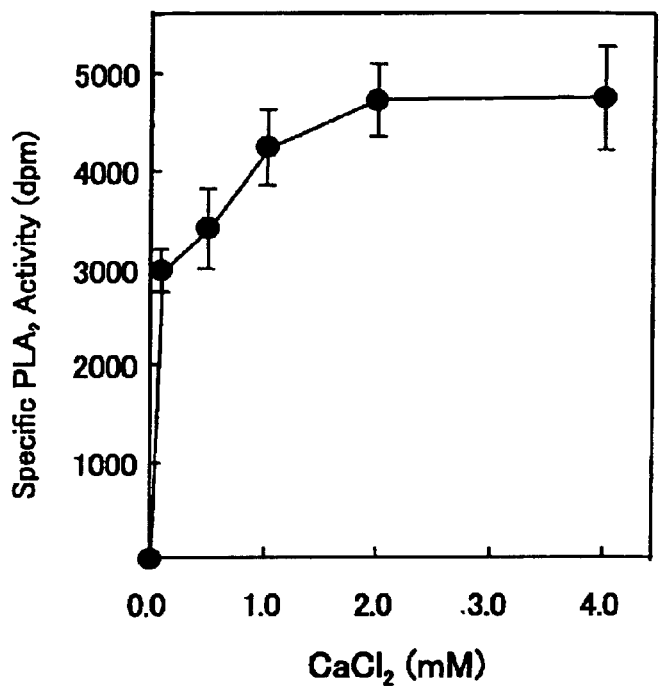
FIG. 3 shows the $Ca^{2+}$ dependence for $PLA_2$ activity in the supernatant of the transformant having the gene encoding the human $PLA_2$ of this invention.

The $PLA_2$ expressing vector was prepared by insertion of this cDNA into pcDNA 3.1(+) (Invitrogen) at the down stream of its promoter in the right direction (the sites between NotI and XbaI sites). The base sequence from the promoter to $PLA_2$ cDNA was determined again to confirm the absence of artificial mutation. Then, the $PLA_2$ expressing vector was inserted into COS-7 cells, the established cell line originated from monkey kidney. Transfection was performed with FuGENE™6 transfection reagent (Boehringer Mannheim) according to the method of the manufacture's instruction. At three days after the transfection, $PLA_2$ activities in the culture supernatant and the cell lysates were measured. Measurement of $PLA_2$ activities was carried out according to the Elsbach et al.'s method (Methods Enzymol. 197, 24–31 (1991)) using 3H-oleate-labeled E. coli membrane phospholipid fractions as the substrate. Significantly high $PLA_2$ activities were detected in the culture supernatant compared with the supernatant in the cultured cells in which a control plasmid with no cDNA of the $PLA_2$ were transfected (FIG. 2). In addition, high concentration of $Ca^{2+}$ was required for the exertion of the enzymatic activities (FIG. 3).

Example 6

Screening for a Compound that Inhibits $PLA_2$ Activity

Inhibitory activity against this novel type of human secretory type $PLA_2$ was determined with Indoxam that is a 1-oxamoylindolidine derivative. It has already been reported that Indoxam inhibits the enzymatic activities of IIA type and IB type secretory type $PLA_2$ (Yokota et al., Biochim. Biophys. Acta (1999) 1438, 213–222). The $PLA_2$ activities were determined by the measurement of the quantity of released $^{14}C$-oleic acid from $^{14}C$-labeled 1-palmitoyl-2-oleoyl-phosphatidylcholine (POPC), according to the Draheim et al.'s method (J. Med. Chem., (1996) 39, 5159–5175). In the solution composed of 50 mM Tris-HCl (pH 8.0), 200 mM NaCl, 2 mM $CaCl_2$, and 1 mg/ml bovine serum albumin, the substrates composed of 1 mM POPC (the mixture of about 100,000 cpm $^{14}C$-POPC and unlabeled POPC) and 3 mM deoxycholic acid were incubated with each secretory $PLA_2$ in the presence of various concentrations of Indoxam at 40° C. for 60 min. Then, the quantity of released $^4C$-oleic acid was measured. Purified materials were used in the case with human IB type (2 ng), IIA type (10 ng) and X type (4 ng). Human V type, IID type and the secretory type $PLA_2$ of this invention (IIE type) were prepared from the culture supernatant of CHO cells that stably express them.

Figure 4:
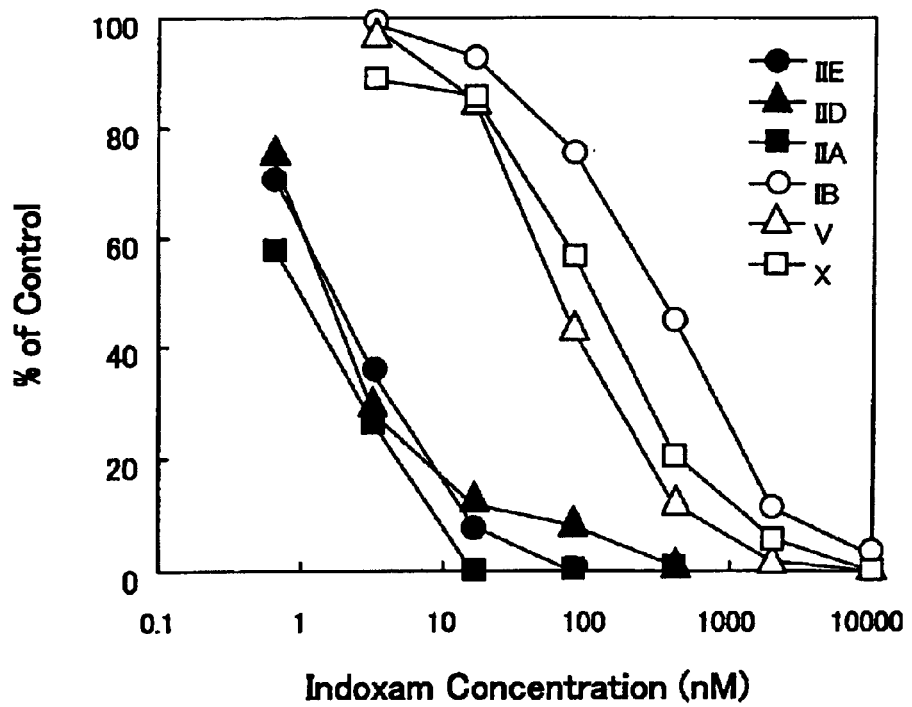
FIG. 4 shows the inhibiting activities for secretory type $PLA_2$ including the human $PLA_2$ of this invention by Indoxam.

The quantity of released $^{14}C$-oleic acid from $^{14}C$-POPC by each human secretory type $PLA_2$ in the absence of Indoxam was regarded as 100% and the quantity of released $^{14}C$-oleic acid in the presence of each concentration of Indoxam was shown as %. As the result, it was conformed that Indoxam strongly inhibits the enzymatic activities of human $PLA_2$ of this invention (IIE type), IID type and IIA type (FIG. 4)

INDUSTRIAL APPLICABILITY

This invention provides human secretory type $PLA_2$; a DNA encoding human secretory type $PLA_2$; a vector including the DNA; a transformant having the vector; a method for producing human secretory type $PLA_2$ using the transformant.

An analytic mean for this secretory type $PLA_2$-related diseases and a screening mean for a specific inhibitory compound against this enzyme are provided by using the secretory type $PLA_2$ of this invention. An assay using an antibody for the enzyme can be applied to the diagnosis of various diseases.

What is claimed is:

1. An isolated polypeptide having phospholipase A2 activity,
   which is encoded by a nucleic acid sequence which hybridizes to the full complement of SEQ ID NO: 29 under stringent conditions,
   wherein stringent conditions comprise heating at 42° C. in 6×SSC, 0.5% SDS and 50% formamide and washing at 68° C. in 0.1×SSC and 0.5% SDS.

2. The isolated polypeptide of claim 1 which is encoded by SEQ ID NO: 29 or by a fragment thereof.

3. The isolated polypeptide of claim 1 which comprises SEQ ID NO: 30.

4. The isolated polypeptide of claim 1 which comprises residues 1 (Asn) to 123 (Cys) of SEQ ID NO: 30.

5. The isolated polypeptide of claim 1 which has been expressed by a prokaryotic cell.

6. The isolated polypeptide of claim 1 which has been expressed by a eukaryotic cell.

7. The isolated polypeptide of claim 1 which has been expressed by an insect cell.

8. The isolated polypeptide of claim 1 which has been expressed by a mammalian cell.

9. The isolated polypeptide of claim 1 in immobilized form.

10. A kit comprising the isolated polypeptide of claim 1.

11. A method for detecting antibody in a sample that binds to phospholipase A2 comprising:

contacting a sample with the isolated polypeptide of claim 1, and determining the amount of antibody binding to said isolated polypeptide.

12. A method for making an antibody that binds to phospholipase A2 comprising:

immunizing an animal with the isolated polypeptide of claim 1.

13. A method for identifying a compound which inhibits phospholipase A2 activity comprising:

contacting a test compound with the isolated polypeptide of claim 1 for a time and under conditions suitable for determining phospholipase activity, determining the amount of phospholipase activity, and comparing the amount of phospholipase activity obtained with the amount of phospholipase activity of the isolated polypeptide in the absence of said test compound.

* * * * *